United States Patent [19]

Toth et al.

[11] 4,075,249

[45] Feb. 21, 1978

[54] 3,4,5-TRIMETHOXY-α-ETHYNYL-BENZHYDROL AS A FUNGICIDALLY EFFECTIVE COMPOUND

[75] Inventors: Edit Toth; Jozsef Törley; Sandor Görög; Laszlo Szporny; Eva Palosi; Szabolcz Szeberenyi, all of Budapest, Hungary

[73] Assignee: Richter Gedeon Vegyeszeti Gyar RT., Budapest, Hungary

[21] Appl. No.: 630,510

[22] Filed: Nov. 10, 1975

Related U.S. Application Data

[62] Division of Ser. No. 495,846, Aug. 8, 1974, Pat. No. 3,965,179.

[30] Foreign Application Priority Data

Aug. 15, 1973 Hungary ................................. RI 520

[51] Int. Cl.$^2$ ................................................ C07C 33/06

[52] U.S. Cl. ........................... 260/613 D; 260/558 A; 260/575; 260/590 C; 260/592; 260/613 R; 71/122

[58] Field of Search ........................ 260/613 R, 613 D

[56] References Cited

U.S. PATENT DOCUMENTS 2,711,384   6/1955   Darley .............................. 260/618 B

OTHER PUBLICATIONS

Dillard et al., "J. Med. Chem.", 10(1), 40–42 (1966).
Purcell et al., "J. Med. Chem.", 11(2), 199–203 (1965).
Cadiot, "Ann. Chim. (France)" 1, 214–229 (1956).
Rauss–Godineau et al., "Bull. Soc. Chim. France", 1966(9), 2885–2892.

*Primary Examiner*—Norman Morgenstern
*Attorney, Agent, or Firm*—Karl F. Ross

[57] ABSTRACT

The new compound 3,4,5-trimethoxy-α-ethynyl benzhydrol which has been found to be an effective fungicide.

1 Claim, No Drawings

3,4,5-TRIMETHOXY-α-ETHYNYL-BENZHYDROL AS A FUNGICIDALLY EFFECTIVE COMPOUND

This is a division of application Ser. No. 495,846, filed Aug. 8, 1974, now U.S. Pat. No. 3,965,179.

The invention relates to a process for the preparation of α-ethynyl, benzohydrals and ring-substituted derivatives thereof, by reacting the corresponding benzophenones with acetylene. The essential feature of the invention is that the reacting of starting benzophenones with acetylene is carried out at atmospheric pressure, at ambient temperature in an aprotic solvent, in the presence of a tertiary alcohol of an alkali metal.

The literature describes several processes for converting benzophenone and substituted derivatives thereof into the corresponding α-ethynyl benzhydrals. The practical performance of these known processes presents, however, many difficulties. The yields are low in consequence of the formation of by-products; the technological procedure is complicated and long reaction times are necessary to obtain satisfactory degrees of conversion.

In a known process, benzophenone is reacted with ethynylene-magnesium bromide (Br-Mg-C≡C-Mg-Br) in the presence of ethyl alcohol (V. K. Teterin and A. P. Ivanov: J. Gen. Chem. USSR. 7, 1629 (1937); in this way tetraphenyl butyne diol is formed as by-product apart from the desired ethynyl benzohydrals. In addition to the difficulties of isolation and low yields (50 to 60 percent) a further drawback of this process is that it is performed in a multiplity of steps: ethyl magnesium bromide is formed first, by reacting magnesium with ethyl bromide; acetylene gas is then introduced into the anhydrous ether solution of the ethyl magnesium bromide until the evolution of ethane gas, and the thus obtained ethynylene magnesium bromide is reacted finally with the benzophenone.

According to another known method (German Patent Specification No. 1 028 561; U.S. Pat. No. 2,957,006) liquid ammonia is cooled by the aid of a mixture of acetone and dry ice to a temperature between −60° C and −70° C; acetylene gas is then introduced into the cooled liquid ammonia, and metallic sodium or potassium is added in minor portions to the reaction mixture. Thereafter, a solution of the benzophenone in anhydrous ether is introduced slowly into the resulting heterogenic reaction mixture. After the end of the reaction, the liquid ammonia is left to evaporate overnight. The reaction mixture is then decomposed with an acid; the desired product is isolated by extraction with ether and then purified further. This process has drawbacks that the use of a special equipment is required for the performance thereof, the process is performed at very low temperature and the technological procedure is extremely dangerous.

There have been described also processes wherein potassium hydroxide was used for the formation of the alkali metal acetylide. According to one specific mode of operation the potassium hydroxide is used in the form of an anhydrous powder, prepared by fusing potassium hydroxide in a nickel cup at high temperature, cooling the melt, gringing and sieving the cake to a fine powder. The thus prepared pulverized potassium is used in a great excess for performing the reaction, in order to shift the reaction equilibrium in the desired direction. This preparation of the potassium hydroxide condensing agent is difficult and requires a multiplicity of operations. The very hydroscopic potassium hydroxide must be handled carefully; all these factors are serious drawbacks in the commercial performance of the process. A further disadvantage is the fact that the required great excess of the potassium hydroxide causes harmful side reactions, such as polymerization and the formation of acetylene glycols (A. J. Zakharova: J. Gen. Chem. USSR., 11, 939 (1941); P. Cadiot: Bull. Soc. Chim. France 1951, 100; P. Cadiot: Ann. Chim. Vol. 13:1, 214(1956); J. Godineau, P. Cadiot: Bull. Soc. Chim. France, Vol. 9, p. 2885 (1966).

In another method of performing the process using potassium hydroxide, the reaction is carried out in a solvent mixture containing primary alcohols. The corresponding ethynyl derivative is obtained at atmospheric pressure with yields of 57–76 %; the ethynyl-content of the product is between 83 % and 95 %. To obtain a product of satisfactory purity, further purification operations must be carried out, whereby the yield is reduced still further. The yield can be increased by working at elevated pressures, but the necessity of pressure-proof equipment and the danger of working with acetylene at higher pressures are serious drawbacks (I. N. Nazarov et al.: Invest. Akad. Nank SSSR., Otdel. Khim. Nank, 1370 (1956); N. N. Libman et al.: Khim Pharm. Zh. Vol. 3, No. 1, p. 3, 31 (1967)).

Japanese workers have used lithium acetylide or an ethylene diamine complex thereof for the ethynylating of benzophenones. Very low yields of 40 % to 67 % were obtained by this process (Hauro Saikachi, Tokujiro Kitegava: Yakugaku Zasshi 89 (11) 1626 (1969).

All the above mentioned drawbacks are completely eliminated by the process of the present invention. It has been found that the conversion of the benzophenones into the corresponding α-ethynyl benzhydrols can be carried out in short time with high yields, at atmospheric pressure, without formation of by-products if the starting benzophenone is reacted with acetone in the presence of a tertiary alcoholate of an alkali metal, in a solvent delivering no protons to the reactants i.e. an aprotic solvent.

The new process of the present invention has the advantage over the known processes outlined above that it is a simple technological procedure which can be easily performed on commercial scale. There is no need to use liquid ammonia; the reaction is carried out at atmospheric pressure, and no special equipment is needed. As a further advantage, the benzophenones can be converted with practically quantitative yield into the corresponding ethynyl benzhydrols. These are obtained in a high degree of purity, so that no special purification processes, such as chromatography, are needed. Another advantage is that benzophenones containing nitro or amino groups as substituents can also be ethynylated with high yields (84 to 90 %), while the known processes give in such cases only yields between 40 % and 70 %.

According to the present invention, the ethynylating of benzophenones is carried out by reacting the benzophenone starting material with acetylene at atmospheric pressure, in the presence of an alkali metal tertiary alcoholate, in a solvent medium delivering no protons.

As alkali metal tertiary alcoholates, especially potassium tertiary alcoholates such as potassium tert.-amylate or preferably potassium tert.-butylate may be used.

As solvent medium delivering no protons, e.g. benzene, toluene, xylene, N,N-dimethyl formamide, N- methyl acetamide, N-methyl pyrrolidone, dimethyl sulphoxide, 1,2-dimethoxy ethane, diethyl ether, dioxane or tetrahydrofuran can be used in the process of the invention. The reaction is carried out preferably in tetrahydrofuran as solvent medium at a temperature between −20° C and +40° C, preferably at 20°–25° C.

The process of the invention can be accomplished preferably in the following way:

Potassium tert.-butylate or tert.-amylate is dissolved within a few minutes in tetrahydrofuran, at room temperature in a nitrogen atmosphere and then acetylene gas is passed through the solution at room temperature, for 30 to 60 minutes. The starting benzophenone, or preferably a tetrahydrofuran solution thereof is then added to the reaction mixture, while the stream of acetylene gas continues to be passed through the reaction mixture. The practically quantitative completion of the ethynylation reaction requires 15 to 60 minutes, depending on the used starting materials. The procedure can be monitored easily by thin layer chromatography. Thereafter the reaction mixture is decomposed by adding a dilute acid or an aqueous solution of ammonium chloride, and the tetrahydrofuran is distilled off. The residual ethynylated benzophenone is recovered from the aqueous phase by filtration or by solvent extraction. The obtained crude product may be purified, if needed, by recrystallization or by distillation.

The new process of the invention can be used favorable for the preparation of new substituted derivatives of α-ethynyl-benzohydrols not described hitherto in the literature. These new products, e.g. the compounds described in the Examples 1 to 10, show valuable pharmacological properties; they exert a blocking or inducing effect, respectively, on the microsomal enzyme system of the liver and have also antiviral and fungicidal effects. Furthermore, these new compounds are valuable starting materials in the synthesis of other biologically active compounds.

The invention is elucidated in the following Examples.

EXAMPLE 1

Acetylene is bubbled through a stirred mixture of 147 g. of potassium-tert.butylate and 600 ml. of tetrahydrofuran for 30 minutes at 20° to 22° C, thereafter a solution of 210 g. of 2,5-dimethyl-benzophenone in 240 ml. of tetrahydrofuran is added to the reaction mixture within 20 minutes. The introduction of acetylene is continued for further 20 minutes, then the reaction mixture is decomposed with an aqueous solution of ammonium chloride. Tetrahydrofuran is distilled off in vacuo, and the separated product is extracted into methylene chloride. The methylene chloride phase is washed until neutral, dried over anhydrous magnesium sulfate, and the solvent is distilled off in vacuo. 231.4 g. (97.8 %) of 2,5-dimethyl-α-ethynyl-benzhydrol, a new compound not described in the literature, are obtained. B.p.: 119°–120° C/0.05 mmHg.

Analysis for $C_{17}H_{16}O$: Calculated: C 86.40 %; H 6.83 %. Found: C 86.29 %; H 7.01 %.

EXAMPLE 2

Acetylene is introduced into a stirred mixture of 56 g. of potassium tert.-butylate and 220 ml. of tetrahydrofuran for 30 minutes at 20° to 22° C, thereafter a tetrahydrofuran solution of 68 g. of 3,4,5-trimethoxy-benzophenone is added to the reaction mixture within 15 minutes. The introduction of acetylene is continued for further 30 minutes, then the reaction mixture is processed as described in Example 3. 70.9 g. (95 %) of 3,4,5-trimethoxy-α-ethynyl benzhydrol, a new compound not described in the literature, are obtained. M.p.: 88° C.

Analysis for $C_{18}H_{18}O_4$: Calculated: C 72.46 %; H 6.08 %. Found: C 75.52 %; H 6.01 %.

What we claim is:
1. 3,4,5-trimethoxy-α-ethynyl-benzhydrol.

* * * * *